United States Patent [19]
Reyburn

[11] Patent Number: 5,926,252
[45] Date of Patent: Jul. 20, 1999

[54] OPHTHALMIC INSTRUMENT THAT MEASURES ROTATION OF A TORIC CONTACT LENS

[76] Inventor: Thomas P. Reyburn, 12i7 E. Maple, Fruitport, Mich. 49415

[21] Appl. No.: 09/140,120

[22] Filed: Aug. 25, 1998

[51] Int. Cl.⁶ .............................. A61B 3/10; G02C 7/04
[52] U.S. Cl. ...................... 351/214; 351/160 R; 351/177
[58] Field of Search ................................ 351/200, 205, 351/214, 211, 160 R, 177, 212, 247

[56] References Cited

U.S. PATENT DOCUMENTS

| | | | |
|---|---|---|---|
| 449,681 | 4/1991 | Lasar | 33/343 |
| 1,415,833 | 5/1922 | Ginsburg | 33/391 |
| 1,532,878 | 4/1925 | Bugbee | 33/343 |
| 1,919,791 | 7/1933 | Larkin | 33/391 |
| 2,464,547 | 3/1949 | Allyn | 351/214 |
| 4,201,226 | 5/1980 | Phillips | 128/774 |
| 4,268,133 | 5/1981 | Fischer | 351/161 |
| 4,309,085 | 1/1982 | Morrison | 351/39 |
| 4,322,139 | 3/1982 | Wichterle | 351/160 |
| 4,358,889 | 11/1982 | Hornbeck | 33/343 |
| 4,901,443 | 2/1990 | Lakhman | 33/391 |
| 4,976,533 | 12/1990 | Hahn | 351/160 |
| 5,038,489 | 8/1991 | Muehlenbein | 33/512 |
| 5,062,701 | 11/1991 | Drazba | 351/160 |
| 5,184,405 | 2/1993 | Cress | 33/1 SD |
| 5,517,259 | 5/1996 | Blum | 351/160 |
| 5,528,321 | 6/1996 | Blum | 351/160 |
| 5,561,482 | 10/1996 | Miyake | 351/208 |
| 5,686,981 | 11/1997 | Anan | 351/212 |
| 5,870,167 | 2/1999 | Knopp et al. | 351/212 |

FOREIGN PATENT DOCUMENTS 2211609  7/1989  United Kingdom .

OTHER PUBLICATIONS

Life–Link Slope Meter, Life–Link International of Jackson Hole, Wyoming, ©1980.

*Primary Examiner*—Huy Mai
*Attorney, Agent, or Firm*—Price, Heneveld, Cooper, DeWitt and Litton

[57] ABSTRACT

An optical diagnostic apparatus for measuring toric contact lens rotation comprising a slit lamp optical instrument including a light source, a slit light projector for projecting a beam of light, and a slit light rotator for rotating the beam of light, a patient head retainer in alignment with the projector to project a slit light beam from the projector onto the eye of a patient and a contact lens on the eye, a slit light rotator actuator for the slit light rotator, for rotating the projected slit light over a range of angles onto the patient's eye and the contact lens thereon, a gravity responsive angle indicator and/or electronic indicator at the slit light rotator, and an arcuate angle scale rotatable with the slit light rotator and cooperable with the indicator to indicate angle of rotation of the angle scale and rotator, whereby the contact lens toric angle can be observed for determining the toric contact lens prescription.

8 Claims, 3 Drawing Sheets

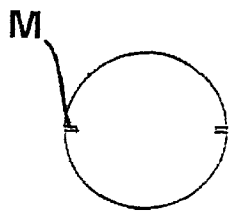
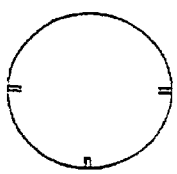
Fig. 3A   Fig. 3B
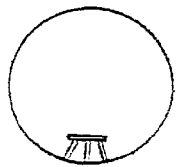
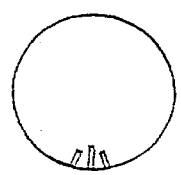
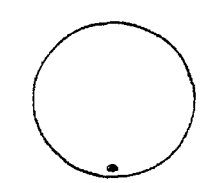
Fig. 3C   Fig. 3D   Fig. 3E
Fig. 4
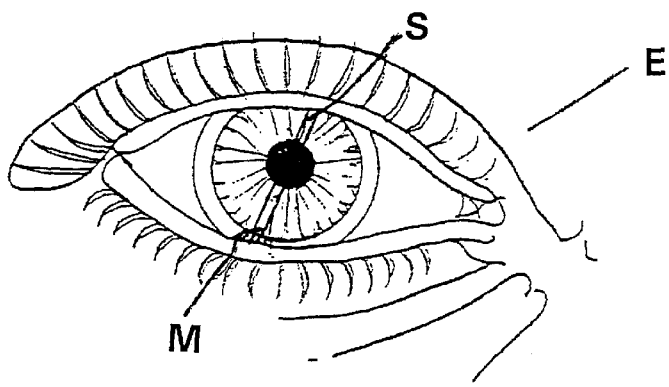
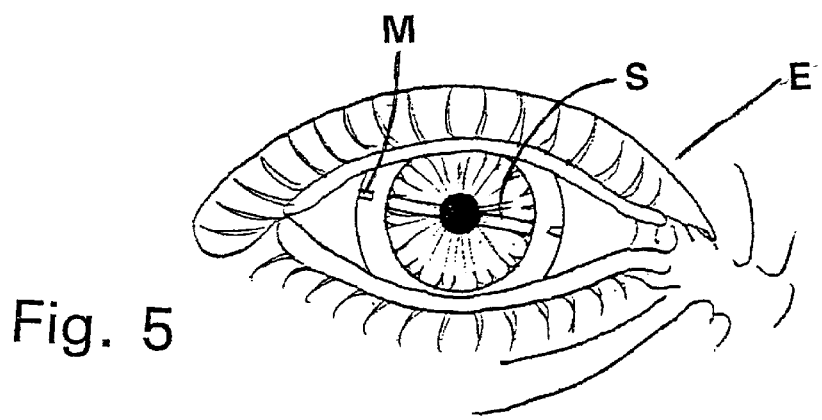
Fig. 5

5,926,252

OPHTHALMIC INSTRUMENT THAT MEASURES ROTATION OF A TORIC CONTACT LENS

BACKGROUND OF THE INVENTION

This invention relates to measurement of the rotation of a corrective toric contact lens.

The characteristic of astigmatism as applied to the eye itself is typically corrected by an asymmetric prescription of the corrective lens, which is called a toric contact lens. If the amount of astigmatism is known, there are known ways of manufacturing the asymmetric lens in order to cause the focus to occur on the retina. Frequently, however, difficulty occurs in the accurate determination of the prescription for the eye of a particular person having astigmatism and wishing to wear contact lenses.

To aid in this determination, contact lens manufacturers are known to create tiny, almost invisible markings such as dots and/or lines on the lens, located at the edges of the convexly curved lens. These markings can be formed by known techniques. With placement of the lens on the cornea of the eye, a care giver or clinician, such as an optometrist, an oculist, or an ophthalmologist, estimates the amount of contact lens rotation on the eye, usually from the horizontal or from the vertical, and prescribes according to the effect the rotation has on the person's astigmatism, the prescription being for a corrective toric contact lens. Such estimates are too often not accurate enough, resulting in errors of undercorrection or overcorrection in lens rotation.

There are two significant areas to address in correcting vision astigmatism, 1) the location in degrees of the astigmatism in the patient's spectral astigmatic prescription, and 2) the amount in degrees of rotation of the toric contact lens while on the eye. The examination lens of the care provider provides the spectral astigmatic prescription location between 0 and 180 degrees. When the degree of rotation of the contact lens is determined, it has to be added to or subtracted from the patient's spectacle prescription to determine the proper toric contact lens prescription. That is, if the contact lens rotation is clockwise, it is called "left add" or "LA." If the lens rotation is counterclockwise, it is called "right subtract" or "RS." This contact lens rotation is caused by eyelid pressure and gravitational pull and other eye conditions. To help prevent contact lens rotation, sometimes prism ballast is added to the lens, and/or or slab off is used.

Techniques and devices have been proposed for more accurately ascertaining the degree of lens rotation, but these are typically inaccurate. Disclosed in the inventor's prior application Ser. No. 08/898,623 entitled METHOD AND APPARATUS FOR MEASURING TORIC CONTACT LENS ROTATION, filed Jul. 22, 1997, is a unique development for determining this characteristic. This present invention provides a further development from that prior invention.

SUMMARY OF THE INVENTION

One version of this present invention provides apparatus and a method of easily, quickly and accurately measuring the rotation of a toric contact lens on the eye of a patient with a combination slit lamp and gravity indicator, this invention enabling the clinician to properly prescribe astigmatism correcting toric contact lenses directly from readings taken from the slit lamp apparatus.

Another version of this invention is to provide an electronically responsive angle indicator of the rotation of a toric contact lens.

These and other features, advantages and objects of the present invention will be further understood and appreciated by those skilled in the art and profession by reference to the following specification, claims and appended drawings.

BRIEF DESCRIPTION OF THE DRAWINGS

FIGS. 3A–3E are diagrammatic views depicting five of the commonly used edge markings on commercially available contact lenses;

FIG. 4 is a diagrammatic front view of an eye with marked contact lens and slit light beam projected thereon; and FIG. 5 is a diagrammatic view of an eye with an alternatively marked contact lens and slit light beam projected thereon.

DETAILED DESCRIPTION OF PREFERRED EMBODIMENTS

Figure 1:
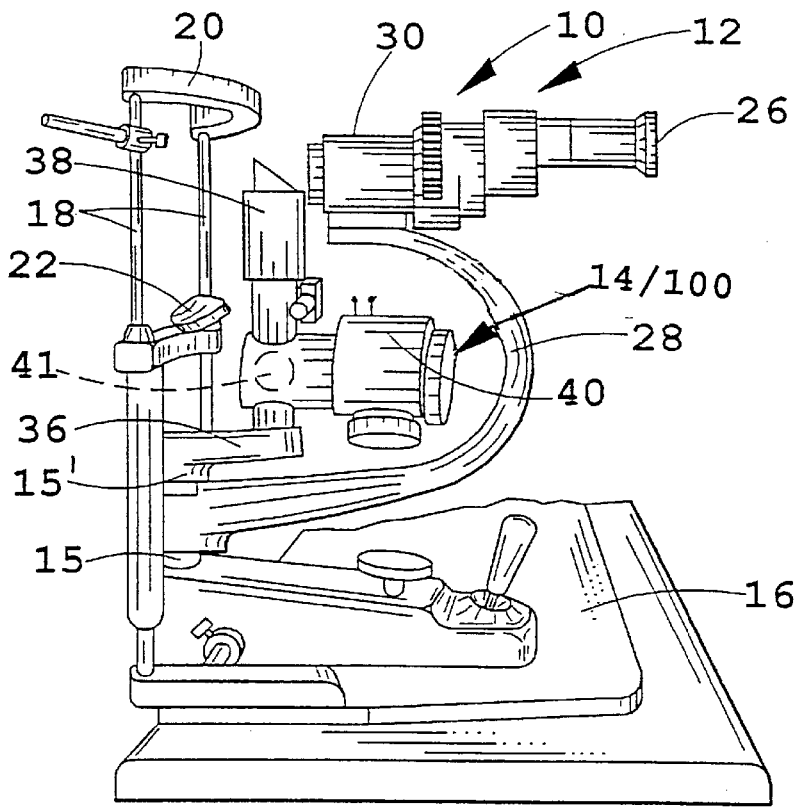
FIG. 1 is a side elevational view of the novel apparatus using one type of slit lamp.

Referring now specifically to the drawings, in FIG. 1 is depicted a version of the novel optical diagnostic apparatus 10 for measuring toric contact lens rotation by combining a slit lamp optical instrument 12 with a gravity responsive angle indicator subassembly 14. The entire apparatus rests upon a suitable base 16. One side of base 16 (left side in FIG. 1) is a patient's side of the apparatus and at the opposite side is the professional or clinician's side of the apparatus. The patient's side has a mechanism for positioning and retention of the patient's head and eyes to be examined while the clinician's side has the eye pieces and adjustment apparatus to enable viewing of the patient's eye and contact lens thereon as well as control of the slit light beam, in a manner to be described. Specifically, one side of base 16 has vertically projecting support rods 18 which mount a forehead retainer 20 and preferably a chin rest 22, both of conventional type. Spaced from these components is a pair of eye pieces 26 on a frame 28 pivotally attached at its lower end 15 to base 16. The eye pieces are optically affiliated with the slit lamp lens assembly 30 of a conventional type for viewing either eye of a patient by slightly pivoting frame 28 on pivot 15 about a vertical axis. Also pivotally mounted at 15 and 15' to base 16 and frame 28 is light arm support 36. On this support is a slit light source 38 of conventional type enabling the optical system to project a slit light beam onto the eye of the patient. The slit lamp, like all slit lamps, enables the slit light beam to rotate on the patient's eye and on any contact lens resting on the eye cornea. In the slit lamp version depicted, drum of barrel 40 is mounted on support 36 and rotatable on a horizontal axis to cause the slit light beam to rotate on the patient's eye and on any contact lens resting on the eye cornea. Other comparable slit lamp adjusting mechanisms may employ, instead of drum 40, a knob 41 (shown in phantom in FIG. 1), or alternative slit light rotating means, as is well known in the optical industry.

Figure 2:
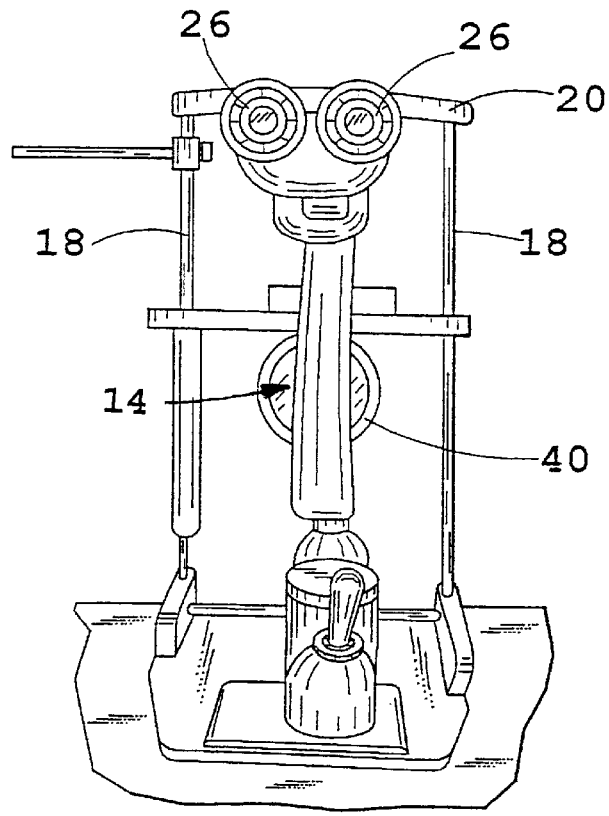
FIG. 2 is an elevational view of the novel apparatus as viewed from the clinician's side.
Figure 2A:
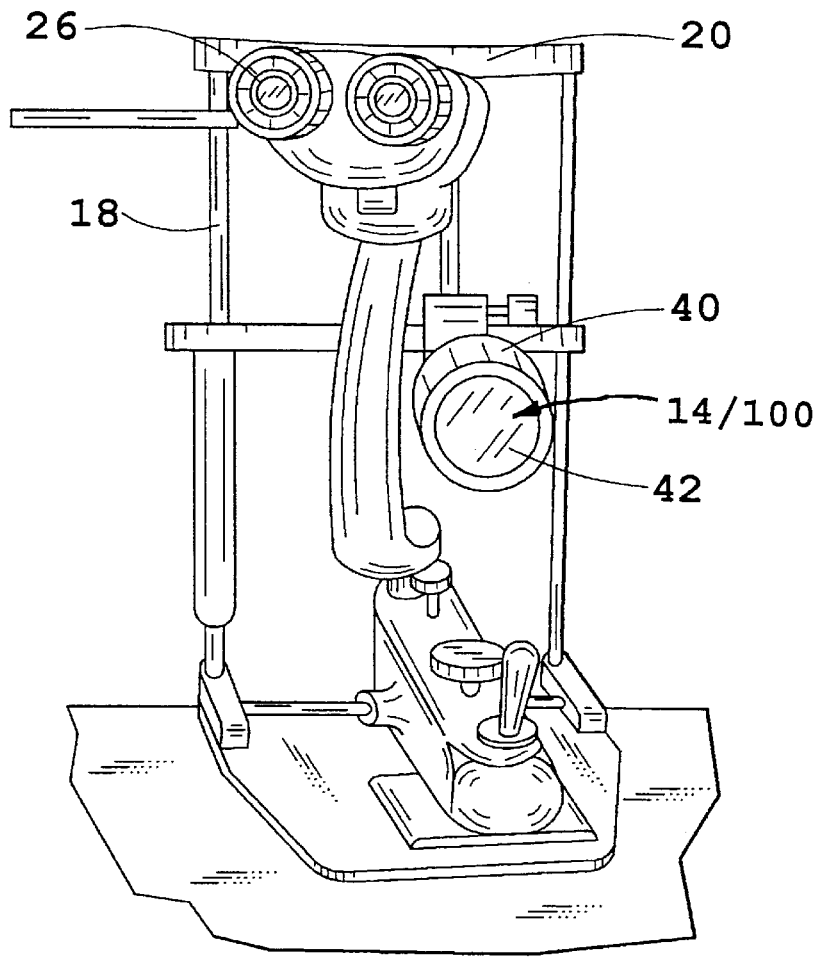
FIG. 2A is an elevational view similar to FIG. 2, but with the clinician's optical instrument pivoted laterally to fully expose the lens angle indicator.
Figure 2B:
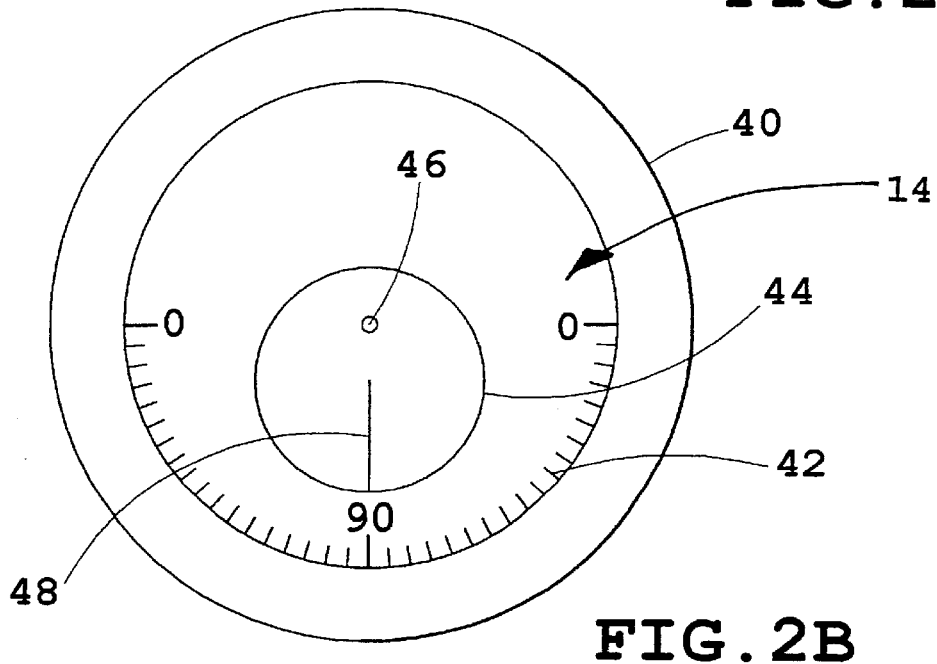
FIG. 2B is an elevational view of the lens angle indicator.

In the depicted embodiment, there is mounted, at the clinician's side of the apparatus, a gravity responsive angle indicator subassembly 14 (FIG. 2) which comprises an arcuate angle scale 42 (FIG. 2B) in a vertical plane on the end of barrel 40, normally encompassing an angular range of 0° to 180°. Some slit lamps may only show a 45° rotation scale before other means are needed to change the adjustments so the clinician can see the rest of the 90° range. In the version illustrated, the bottom of the scale at a true vertical orientation is designated 90° while the two opposite ends of the scale on a horizontal plane are designated 0° and 180° Alternatively, the 180° designation could be at the horizontal plane and the 0° designation at the vertical orientation. This scale moves angularly through orientation changes with angular rotation of barrel 40. On the end of barrel 40, centrally of the scale 14, is an indicator or pointer 48, here shown to include a housing 44, and pivotally mounted at point 46 at the center of the scale. Line indicator 48 extends vertically downwardly from pivot point 46 in response to gravity. Indicator line 48 is integral with the housing bubble 44 to move therewith. Alternative mounting of the gravity indicator may be made, although this depicted version is simplistically shown and preferred for the drum type slit lamp rotation shown.

Toric contact lenses are marked in various fashions by the manufacturer as indicated by examples in FIGS. 3A–3E. That is, the inscribed markings at the peripheral edge of the lens may be equatorially arranged at opposite sides of the lens as in FIG. 3A, or in three different locations at 90° and 180° from each other as in FIG. 3B, in a three legged angular arrangement at one edge area of the lens as in FIG. 3C or FIG. 3D, or as a dot as illustrated at the edge of the lens in FIG. 3E. These are only some of the ways manufacturers mark their toric contact lenses. When the lens is placed on the eye E (FIG. 4 or FIG. 5), at least one marking M should be visible to the clinician when viewing the eye through the eye pieces and optical system. The clinician will observe the location of the marking and align the slit lamp beam of light S projected onto the eye and contact lens.

In use of the novel apparatus, the diagnostic contact lens having a reference indication line or mark thereon is placed on the eye. The patient's head is positioned with the forehead against support 20 and preferably the chin in place on chin rest 22, the eyes being oriented directly toward optical system 30. The slit light unit is activated so that a narrow beam of light S from the slit lamp is directed onto the lens of the eye in the fashion indicated in FIGS. 4 or 5. The narrow light beam is then rotated by, in this example, rotation of barrel 40, until the light slit is aligned with the scribe mark on the contact lens. The toric angle instrument always indicates vertically straight up or down due to gravity at indicator line 48. With the slit lamp beam aligned with a scribe mark on the contact lens, the clinician can read on scale 42 the degrees of contact lens rotation on the eye. This degree of rotation is easily and accurately read by the clinician and is used to determine the contact lens prescription as it relates to the aspherical portion of the prescription.

An alternative variation of the apparatus incorporates an electronic sensor 100 (FIG. 1) on the slit lamp in place of the visual scale and indicator. This sensor electronically activates and displays a digital readout of the angle of slit lamp beam's rotation on a screen (not shown) to be viewed by the clinician. Such an electronic sensor/indicator apparatus need not depend on a gravity responsive indicator. A representative electronic sensor is that known as OEM Inclinometer marketed by Smart Tool Technologies, a division of Macklanburg-Duncan Co. of San Jose, Calif.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

What is claimed is:

1. An optical diagnostic apparatus for measuring toric contact lens rotation comprising:

a slit lamp optical instrument including a light source, a slit light projector for projecting a beam of light, and a slit light rotator for rotating the beam of light;

said optical instrument having a patient head retainer in alignment with said projector;

said head retainer and said slit light projector being arranged relative to each other to project a slit light beam from said projector onto the eye of a patient at said head retainer and onto a contact lens on said eye;

a slit light rotator actuator for said slit light rotator, for rotating the projected slit light over a range of angles onto the patient's eye and the contact lens thereon; and a responsive angle indicator operably associated with said slit light rotator and cooperable to indicate the contact lens rotation, for determining the patient's prescription.

2. The optical diagnostic apparatus in claim 1 wherein said slit lamp optical instrument includes a patient's side and a clinician's side, and said indicator is at said clinician's side of said instrument.

3. The optical diagnostic apparatus in claim 1 wherein said responsive angle indicator is gravity responsive.

4. The optical diagnostic apparatus in claim 1 wherein said responsive angle indicator is electronically actuated.

5. An optical diagnostic apparatus for measuring toric contact lens rotation comprising:

a slit lamp optical instrument including a light source, a slit light projector for projecting a beam of light, and a slit light rotator for rotating the beam of light;

said optical instrument having a patient head retainer in alignment with said projector;

said head retainer and said slit light projector being arranged relative to each other to project a slit light beam from said projector onto the eye of a patient at said head retainer and onto a contact lens on said eye;

a slit light rotator actuator for said slit light rotator, for rotating the projected slit light over a range of angles onto the patient's eye and the contact lens thereon for alignment with a marking on said lens; and a gravity responsive angle indicator operably associated with said slit light rotator, and an arcuate angle scale rotatable with said slit light rotator and cooperable with said indicator to indicate angle of rotation of said angle scale and said rotator, whereby the contact lens toric angle can be observed for determining the toric contact lens prescription for the patient's eye.

6. The optical diagnostic apparatus in claim 5 wherein said slit lamp optical instrument includes a patient's side and a clinician's side, and said gravity responsive indicator is at said clinician's side of said instrument.

7. The optical diagnostic apparatus in claim 5 wherein said patient head retainer comprises a forehead retainer.

8. The optical diagnostic apparatus in claim 7 wherein said patient head retainer also includes a chin rest.

\* \* \* \* \*